US006520918B1

United States Patent
Stergiopoulos et al.

(10) Patent No.: US 6,520,918 B1
(45) Date of Patent: Feb. 18, 2003

(54) METHOD AND DEVICE FOR MEASURING SYSTOLIC AND DIASTOLIC BLOOD PRESSURE AND HEART RATE IN AN ENVIRONMENT WITH EXTREME LEVELS OF NOISE AND VIBRATIONS

(75) Inventors: Stergios Stergiopoulos, Toronto (CA); Amar C. Dhanantwari, North York (CA)

(73) Assignee: Her Majesty the Queen in Right of Canada as represented by the Minister of National Defence, Ottawa (CA)

( * ) Notice: Subject to any disclaimer, the term of this patent is extended or adjusted under 35 U.S.C. 154(b) by 0 days.

(21) Appl. No.: 09/718,515

(22) Filed: Nov. 24, 2000

(30) Foreign Application Priority Data

Nov. 24, 1999 (CA) .............................. 2290247

(51) Int. Cl.[7] .............................. A61B 5/02
(52) U.S. Cl. .................. 600/490; 600/485; 600/586
(58) Field of Search .............................. 600/485, 490, 600/586

(56) References Cited

U.S. PATENT DOCUMENTS

| | | | | |
|---|---|---|---|---|
| 4,005,701 A | * | 2/1977 | Aisenberg et al. | 600/493 |
| 4,105,020 A | * | 8/1978 | Matsuoka et al. | 600/495 |
| 4,928,705 A | * | 5/1990 | Sekhar et al. | 600/586 |
| 5,135,003 A | * | 8/1992 | Souma | 600/493 |
| 5,309,922 A | * | 5/1994 | Schechter et al. | 600/534 |
| 5,467,755 A | * | 11/1995 | Callahan et al. | 600/528 |
| 5,467,775 A | * | 11/1995 | Callahan et al. | 600/528 |
| 5,662,105 A | * | 9/1997 | Tien | 600/336 |
| 5,680,868 A | | 10/1997 | Kahn et al. | |
| 5,853,005 A | * | 12/1998 | Scanlon | 128/662.03 |
| 5,873,836 A | * | 2/1999 | Kahn et al. | 600/493 |
| 6,179,783 B1 | * | 1/2001 | Mohler | 600/485 |

OTHER PUBLICATIONS

Stergios Stergiopoulos, "Limitations on Towed–array Gain Imposed by a Nonisotropoic Ocean", Journal of Acoustic Society of America, Dec. 1991, pp 3161–3172, vol. 90 (6).
Stergios Stergiopoulos, "Implementation of Adaptive and Synthetic–Aperture Processing Schemes in Integrated Active–Passive Sonar Systems", Proceedings of the IEEE, Feb. 1998, pp 358–396, vol. 86, No. 2.

* cited by examiner

*Primary Examiner*—Robert L. Nasser
*Assistant Examiner*—Patricia Mallari
(74) *Attorney, Agent, or Firm*—Freedman & Associates

(57) ABSTRACT

A method and a device for measuring systolic and diastolic blood pressure and heart rate in an environment comprising extreme levels of noise and vibrations is disclosed. Blood pressure signals corresponding to the heart beat are detected using a first acoustic sensor placed on a patient near an artery. A second acoustic transducer is placed on the patient away from the artery for detecting noise and vibrations. Pressure is applied to the artery forcing the artery to close. The pressure is then reduced and while reducing the pressure the acoustic signals detected by the first and second acoustic sensor as well as a signal indicative of the pressure applied to the artery are provided to a processing unit. The signal of the first acoustic sensor is then processed using an adaptive interferer canceller algorithm with the signal of the second acoustic sensor as interferer. From the processed signal heart beat pulses are determined and relating the heart beat pulses to the pressure signal provides the systolic and diastolic blood pressure. Use of the adaptive interferer canceller provides good results for measurements performed under extreme levels of noise and vibrations such as aboard a helicopter.

19 Claims, 4 Drawing Sheets

METHOD AND DEVICE FOR MEASURING SYSTOLIC AND DIASTOLIC BLOOD PRESSURE AND HEART RATE IN AN ENVIRONMENT WITH EXTREME LEVELS OF NOISE AND VIBRATIONS

FIELD OF THE INVENTION

This invention relates generally to the field of blood pressure monitoring methods and devices and more particularly to auscultatory blood pressure monitoring methods and devices employing means for removing noise and vibration effects from audible heart beat sounds.

BACKGROUND OF THE INVENTION

The blood pressure in the brachial artery is not constant, but varies with time in relation to the beating of the heart. Following a contraction of the heart to pump blood through the circulatory system, the blood pressure increases to a maximum level known as the systolic blood pressure. The minimum blood pressure between heartbeats is known as the diastolic blood pressure.

The traditional technique for measuring the blood pressure of a patient employs an inflatable pressure cuff wrapped around an upper arm of a patient whose blood pressure is to be determined. As the pressure cuff is inflated, cuff pressure and pressure applied to the arm of the patient increases. If the pressure applied to the arm is increased beyond the highest blood pressure in the brachial artery located in the arm beneath the pressure cuff, the artery will be forced to close.

As the pressure in the inflatable cuff is reduced from a high level above the systolic blood pressure, where the brachial artery is permanently closed, to a level below the systolic blood pressure level, the brachial artery beneath the cuff will begin to open and close with each heart beat as the blood pressure first exceeds the cuff pressure and then falls below the cuff pressure. As the blood pressure exceeds the cuff pressure, the artery will open, and a low frequency blood pressure sound corresponding to the heart beat can be detected. This sound is detected using a stethoscope or microphone placed near the down-stream end of the cuff on the patient's arm. The highest cuff pressure at which the heart beat sounds are detectable thus corresponds to the systolic blood pressure of the patient.

As the cuff pressure is reduced further, the cuff pressure will be brought below the diastolic blood pressure. At this pressure level, the brachial artery beneath the cuff remains open throughout the heart beat cycle. Blood pressure sounds, caused by the opening of the artery will, therefore, not be produced. The lowest cuff pressure at which the blood pressure sounds can be detected thus corresponds to the diastolic blood pressure of the patient. The determination of blood pressure based on the detection of the onset and disappearance of blood pressure sounds as varying pressures are applied to an artery, is known as auscultatory blood pressure determination.

In manual auscultatory blood pressure measurement methods, a stethoscope is used to detect the onset and disappearance of the blood pressure sounds. Thus, the blood pressure measurement is highly dependent on the skill and hearing ability of the person taking the measurement. To overcome this dependence on human skill and judgement, and to automate the process of determining a patient's blood pressure, automatic blood pressure monitoring systems based on the auscultatory method of blood pressure determination have been developed. These automatic systems employ one or more microphones placed in or under an inflatable cuff to detect blood pressure sounds.

However, it is almost impossible to detect the blood pressure sounds in a noisy environment such as a moving ambulance, helicopter, airplanes, or naval vessels.

Pneumatic systems measuring pressure variations caused by blood flowing through the artery instead of sound are not sensitive to noise, but extremely sensitive to movement and vibrations. Pressure variations caused by patient movement and any vibrations present are generally much larger than the pressure variations by the blood flow thus rendering these systems useless in the environments mentioned above.

Some blood pressure monitoring systems employ two microphones for detecting blood pressure sounds. For example, two microphones may be placed under the inflatable cuff separated by a distance such that a low frequency blood pressure sound will reach the first microphone 180 degrees out of phase from the second microphone. Noise signals will tend to reach each microphone essentially simultaneously, and in phase. Therefore, subtracting the two microphone signals from each other will tend to enhance the useful data and diminish unwanted noise. The two microphone signals can be added and subtracted from each other to create signal and noise detection thresholds. Microphone signals are considered to be valid blood pressure sound detections if they meet the detection thresholds. These blood pressure monitoring methods tend obtain useful data in moderately noisy environments. However, these systems are less effective when confronted with significant noise levels.

In U.S. Pat. No. 5,680,868 issued to Kahn et al. in Oct. 28, 1997 a method and apparatus for monitoring the blood pressure of a patient by detecting low frequency blood pressure sounds in the presence of significant noise levels is disclosed. Kahn discloses two microphones placed over the brachial artery of a patient to detect the onset and disappearance of blood pressure sounds in the artery as the pressure on the artery is varied. The microphones are placed on the patient separated by a distance such that a true blood pressure sound will preferably be picked up at the second microphone approximately 180 degrees out of phase with respect to the blood pressure sound picked up by the first microphone. The shift in phase between the signals from the two microphones is used to indicate the detection of a blood pressure sound in the presence of significant noise levels. However, the phase detection method is still affected by vibrations detected out of phase at the two microphones. This method is based on the assumption that noise and vibrations are detected at both microphones without a phase shift whereas the blood pressure sound has a phase shift of approximately 180 degrees. Vibrations due to body motion such as shivering or ambient vibrations imposed on the body will generally be detected out of phase at the two microphones making it difficult to detect the beginning and end of a blood pressure sound signal as the pressure cuff deflates. Furthermore, this method requires an extensive amount of computation making it difficult to manufacture a portable device using this method. Another disadvantage of this method is that it is not possible to obtain directly from the processed signals a heart rate, which provides live saving information in emergency situations.

It is an object of the invention to provide a method and a device for measuring systolic and diastolic blood pressure in environments comprising extreme levels of noise and vibration, which overcomes the aforementioned problems.

It is further an object of the invention to provide a method and a device for measuring systolic and diastolic blood pressure in environments comprising extreme levels of noise and vibration that also provides information about the heart rate.

It is yet another object of the invention to provide a method and a device for measuring systolic and diastolic blood pressure in environments comprising extreme levels of noise and vibration enabling accurate measurement of blood pressure during low flow states, such as cardiogenic shock.

It is yet another object of the invention to provide a device for measuring blood pressure in environments comprising extreme levels of noise and vibration that is battery operated and portable.

SUMMARY OF THE INVENTION

In accordance with the present invention there is provided, a method and device for measuring systolic and diastolic blood pressure and heart rate in environments with extreme levels of noise and vibrations. Sensing only noise and vibrations and subtracting it from a measured blood pressure signal using an adaptive interferer canceller provides good results even under extreme conditions such as aboard a helicopter.

In accordance with the present invention there is provided, a method for measuring systolic and diastolic blood pressure of a patient comprising the steps of:

sensing blood pressure signals corresponding to heart beat using a first acoustic sensor placed on the patient near a location of an artery of the patient, the first acoustic sensor for producing a first acoustic signal in dependence upon the blood pressure signals;

sensing noise and vibrations using a second acoustic sensor placed on the patient at a location away from an artery, the second sensor for producing a second acoustic signal in dependence upon noise and vibrations;

sensing pressure applied to the artery using a pressure transducer for sensing pressure and for providing a pressure signal in dependence upon the sensed pressure;

providing the first acoustic signal, the second acoustic signal and the pressure signal to a processing unit while the pressure is applied to the artery;

processing the first acoustic signal for removing interference due to noise and vibrations in the first acoustic signal by subtracting the second acoustic signal from the first acoustic signal using an adaptive interferer canceller algorithm;

detecting heart beat pulses within the processed first acoustic signal; and, determining systolic and diastolic pressure by relating the detected heart beat pulses to the pressure signal.

In accordance with another aspect of the present invention there is provided, a method for monitoring heart beat of a patient comprising the steps of:

sensing blood pressure signals corresponding to heart beat using a first acoustic sensor placed on the patient near a location of an artery of the patient, the first acoustic sensor for producing a first acoustic signal in dependence upon the blood pressure signals;

sensing noise and vibrations using a second acoustic sensor placed on the patient at a location away from an artery, the second sensor for producing a second acoustic signal in dependence upon noise and vibrations;

providing the first acoustic signal and the second acoustic signal to a processing unit;

removing interference due to noise and vibrations in the first acoustic signal by subtracting the second acoustic signal from the first acoustic signal using an adaptive interferer canceller algorithm;

detecting heart beat pulses within the first acoustic signal; and, determining a heart rate from the detected heart beat pulses.

In accordance with the present invention there is further provided, a device for measuring systolic and diastolic blood pressure of a patient in an environment with extreme levels of noise and vibration, the device comprising:

a pressure cuff for applying pressure to an artery of the patient;

a pressure transducer for providing a pressure signal in dependence upon the pressure applied to the artery;

a first acoustic sensor for producing a first acoustic signal in dependence upon blood pressure signals corresponding to heart beat;

a second acoustic sensor for producing a second acoustic signal in dependence upon noise and vibration; and, a processing unit for processing the first acoustic signal using the second acoustic signal in an adaptive interference canceller algorithm, for detecting heart beat pulses within the processed first acoustic signal and for determining systolic and diastolic blood pressure using the detected heart beat pulses and the pressure signal.

BRIEF DESCRIPTION OF THE DRAWINGS

Exemplary embodiments of the invention will now be described in conjunction with the following drawings, in which.

DETAILED DESCRIPTION

Figure 1:
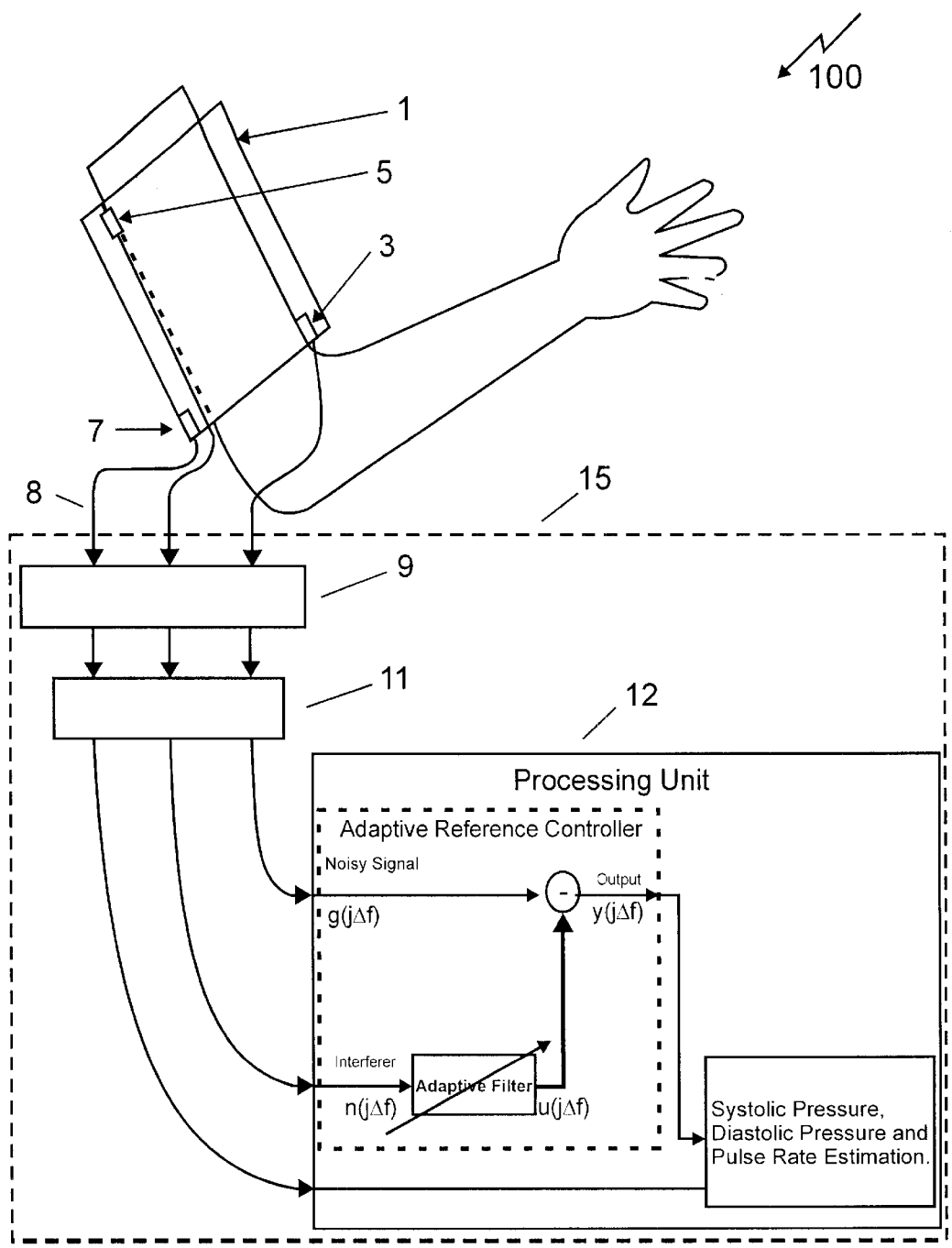
FIG. 1 is a simplified diagram of a device for measuring systolic and diastolic blood pressure in environments comprising extreme levels of noise and vibration according to the invention.

FIG. 1 illustrates schematically a device 100 for measuring systolic and diastolic blood pressure—sphygmomanometer—in environments comprising high levels of noise and vibration according to the invention. The device 100 comprises a pressure cuff 1 to be wrapped around an upper arm of a patient whose blood pressure is to be determined. Within the pressure cuff 1 is a primary acoustic sensor 3 for capturing blood pressure sound, a secondary acoustic sensor 5 for capturing ambient noise and vibrations and a pressure transducer 7 for measuring cuff pressure. The primary acoustic sensor 3 is located on the brachial artery of the upper arm at the down—stream end of the pressure cuff 1. The secondary acoustic transducer 5 is located away from the brachial artery in order to capture only noise and vibrations superposed to the blood pressure sound signal detected by the primary acoustic sensor 3. The pressure cuff 1 is connected via a communication link 8 to a housing 15 comprising means for signal conditioning 9 such as filtering, an A/D converter 11 and a processing unit 12.

In operation the pressure cuff 1 wrapped around an upper arm of the patient is inflated to a pressure beyond the highest blood pressure in the brachial artery forcing the artery to close. The pressure cuff 1 is inflated manually or by a motor driven pump.

As the pressure in the inflatable cuff is reduced to a level below the systolic blood pressure level, the brachial artery beneath the cuff will begin to open and close with each heart beat as the blood pressure first exceeds the cuff pressure and then falls below the cuff pressure. The arterial wall acts in a non-linear fashion with respect to the blood pressure level. Thus, as the blood pressure exceeds the cuff pressure, the artery will open, producing a low frequency blood pressure sound corresponding to the heart beat. This sound is then detected using the primary acoustic sensor 3. Therefore, the pressure detected by the pressure transducer 7 at the time instance when a first blood pressure sound is detected is the systolic blood pressure.

As the cuff pressure is reduced further, the cuff pressure will be brought below the diastolic blood pressure. At this pressure level, the brachial artery beneath the cuff remains open throughout the heart beat cycle. Blood pressure sounds, caused by the opening of the artery will, therefore, not be produced. The lowest cuff pressure at which the blood pressure sounds are detected thus corresponds to the diastolic blood pressure.

During deflation of the pressure cuff 1 ambient noise and vibrations are detected using the secondary acoustic sensor 5. Sensor signals produced by the acoustic sensors 3 and 5 and the pressure transducer 7 are transmitted via the communication link 8 to the housing 15 for processing.

Figure 2:
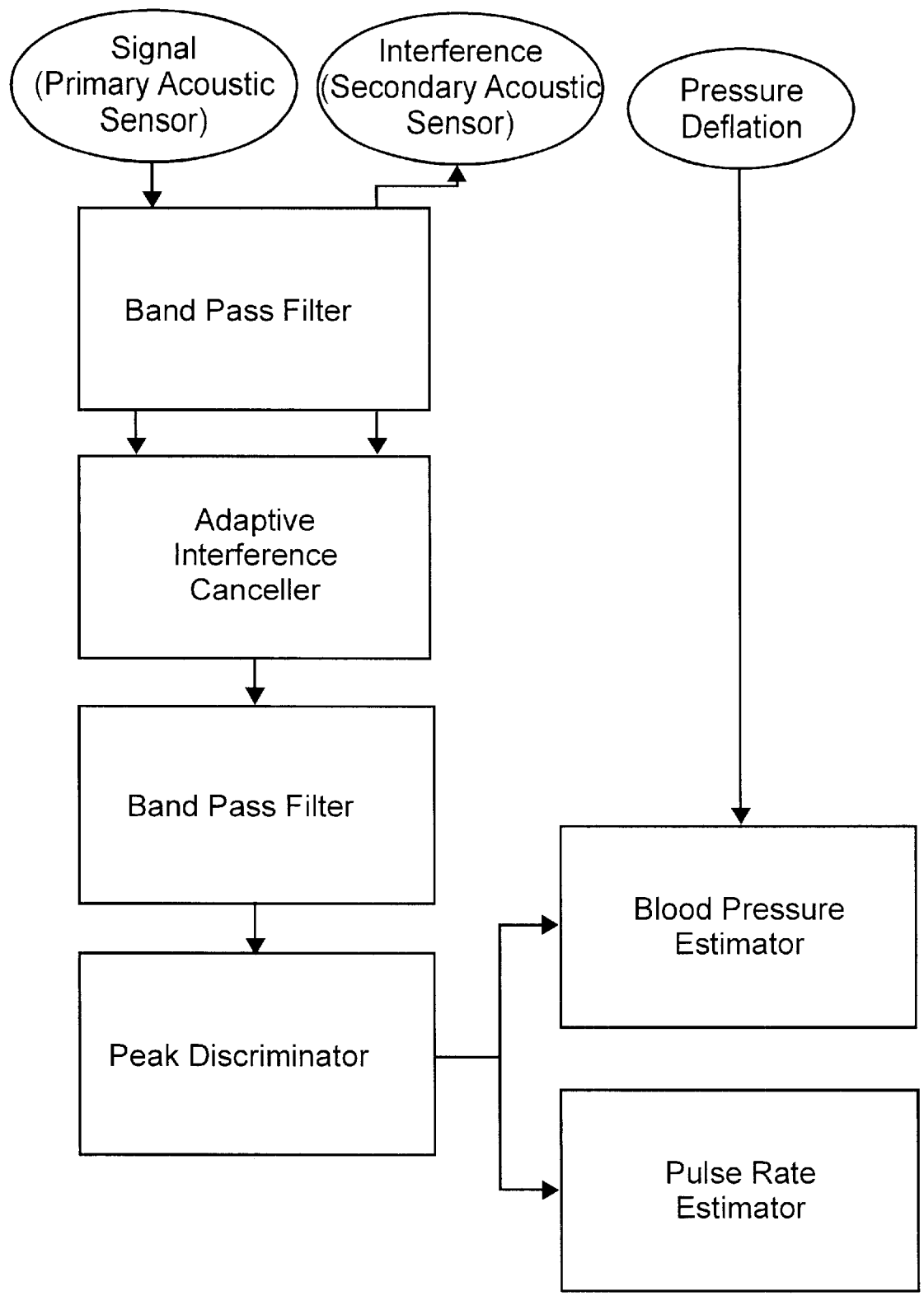
FIG. 2 is a simplified diagram of a signal processing structure according to the invention.

The signals are then processed according to the invention as shown in FIG. 2. In a first optional step the sensor signals are processed in signal conditioning means 9 such as a band pass filter. Since the frequency range of the acoustic signal of interest is well localized using a band pass filter is a useful step for removing excess noise outside this frequency range. The filtered signals are then converted into corresponding digital signals using an A/D converter 11 for provision to the processing unit 12 such as a microprocessor. In the processing unit 12 the acoustic sensor signals are then processed using an adaptive interferer canceller, indicated in FIG. 1 by dotted lines, in order to remove any interference $n(j\Delta t)$—detected by the secondary acoustic sensor 5—from the noisy measured signal $s(j\Delta t)$—detected by the primary acoustic sensor 3. The noisy measured signal $s(j\Delta t)$ is provided to the adaptive interferer canceller as input signal. The signal $n(j\Delta t)$ provided by the secondary acoustic sensor 5 is provided to an adaptive filter of the adaptive interferer canceller as an interference noise signal. The output of the adaptive filter $u(j\Delta t)$ for the interferer input $n(j\Delta t)$ is given by equation (1):

$$u(j\Delta t) = \sum_{i=1}^{L} w_i^{j\Delta t} \times n\left(\left(j+i-\frac{L}{2}\right)\Delta t\right), \qquad (1)$$

$$(i = 1, 2, \ldots L), \quad (j = 1, 2, \ldots K),$$

wherein L is the number of adaptive weights $(w_1, w_2, \ldots w_L)$ at time $j\Delta t$ and K is the maximum number of samples to be processed. The adaptive weights for the adaptive weight algorithm (1) are given by the adaptive weight update equations (2):

$$w_i^{(j+1)\Delta t} = w_i^{j\Delta t} + \left(\frac{\lambda}{\alpha + |n|} \times n\left(\left(j+i-\frac{L}{2}\right)\Delta t\right) \times y(j\Delta t)\right), \qquad (2)$$

$$(i = 1, 2, \ldots L), \quad (j = 1, 2, \ldots K),$$

wherein $\lambda$ is an adaptive step size parameter, $\alpha$ is a stability parameter and $|n|$ is the Euclidean norm of the vector:

$$\left[n\left(\left(j+1-\frac{L}{2}\right)\Delta t\right), n\left(\left(j+2-\frac{L}{2}\right)\Delta t\right), \ldots n\left(\left(j+\frac{L}{2}\right)\Delta t\right)\right].$$

The output of the adaptive interferer canceller is then given by $y(j\Delta t)=s(j\Delta t)-u(j\Delta t)$. In order to calculate the adaptive weight for a sample $(j+1)\Delta t$ to be processed the output of the interferer canceller of the previous sample $j\Delta t$ is used as can be seen in the adaptive weight update equation (2).

This algorithm is an ideal tool for removing any noise and vibration effects in a measured signal if an interferer is accurately measured. The noise measured by the second acoustic sensor 5 placed away from the brachial artery is treated as the interferer $n(j\Delta t)$ and an adaptive weighted signal $u(j\Delta t)$ is then subtracted from the measured acoustic signal of the blood pressure sound $s(j\Delta t)$. Detailed information concerning the adaptive interferer canceller are disclosed by the inventor in "Limitations on towed-array gain imposed by a nonisotropic ocean", published in Journal of Acoustic Society of America, 90(6), 3131–3172, 1991, and in "Implementation of Adaptive and Synthetic-Aperture Processing Schemes in Integrated Active-Passive Sonar Systems", published in Proceedings of the IEEE, 86(2), 358–396, February 1998.

The adaptive interferer canceller has been found to be a powerful tool for removing interference noise from a "noisy" signal if the interference is accurately measured. Furthermore, the adaptive interferer canceller as applied in the device and method for measuring blood pressure according to the invention requires only a minimum amount of computation in order to provide good results even for signals detected in environments with extreme noise and vibration levels.

Optionally, to further reduce noise effects the output signal $y(j\Delta t)$ may be band pass filtered.

The output signal $y(j\Delta t)$ is then provided to a peak discriminator in order to extract valid peaks resulting from heartbeats in the acoustic signal $y(j\Delta t)$ from any background noise. In a first step peaks greater than a noise floor level determined by the peak discriminator are isolated. The isolated peaks are then further examined in order to determine if they satisfy periodicity and constancy in repetition, that is beats are not missing, as is expected from heartbeats. Peaks not satisfying these constraints are discarded. The output of the peak discriminator is a series of constantly repeating periodic peaks. This process also eliminates random peaks due to strong transient noise effects. As is obvious to a person of skill in the art, there are numerous methods for detecting peaks. The method described above has been found to produce good results even in environments with extreme high noise and vibration levels while the required computation is kept to a minimum.

From the results of the peak discriminator a pulse rate estimator determines the immediately available pulse rate of the patient.

The output of the peak discriminator is also provided to a blood pressure estimator. The systolic blood pressure is defined as the blood pressure when the first heartbeat is detected as the pressure duff 1 is deflating. The diastolic blood pressure is defined as the blood pressure when the last heartbeat is detected. From the results of the peak discriminator the time instances where these two pulse peaks occur are determined and then used as a reference to the signal acquired by the pressure transducer 7. The signal acquired by the pressure transducer 7 provides a measurement of the pressure in the deflating pressure cuff 1 as a function of time.

The corresponding pressures at these time instances are the systolic blood pressure and the diastolic blood pressure, respectively.

Alternatively, the measurements are taken while the pressure cuff is being inflated. This method has the advantage that the pressure cuff is inflated to a pressure only slightly above the systolic blood pressure whereas in the above method the pressure cuff is inflated to a pressure much higher than the actual systolic blood pressure in order to ensure closure of the brachial artery.

Furthermore, a plurality of acoustic sensors may be used for each of detecting blood pressure signals and interference noise in order to further improve signal quality.

Figure 3:
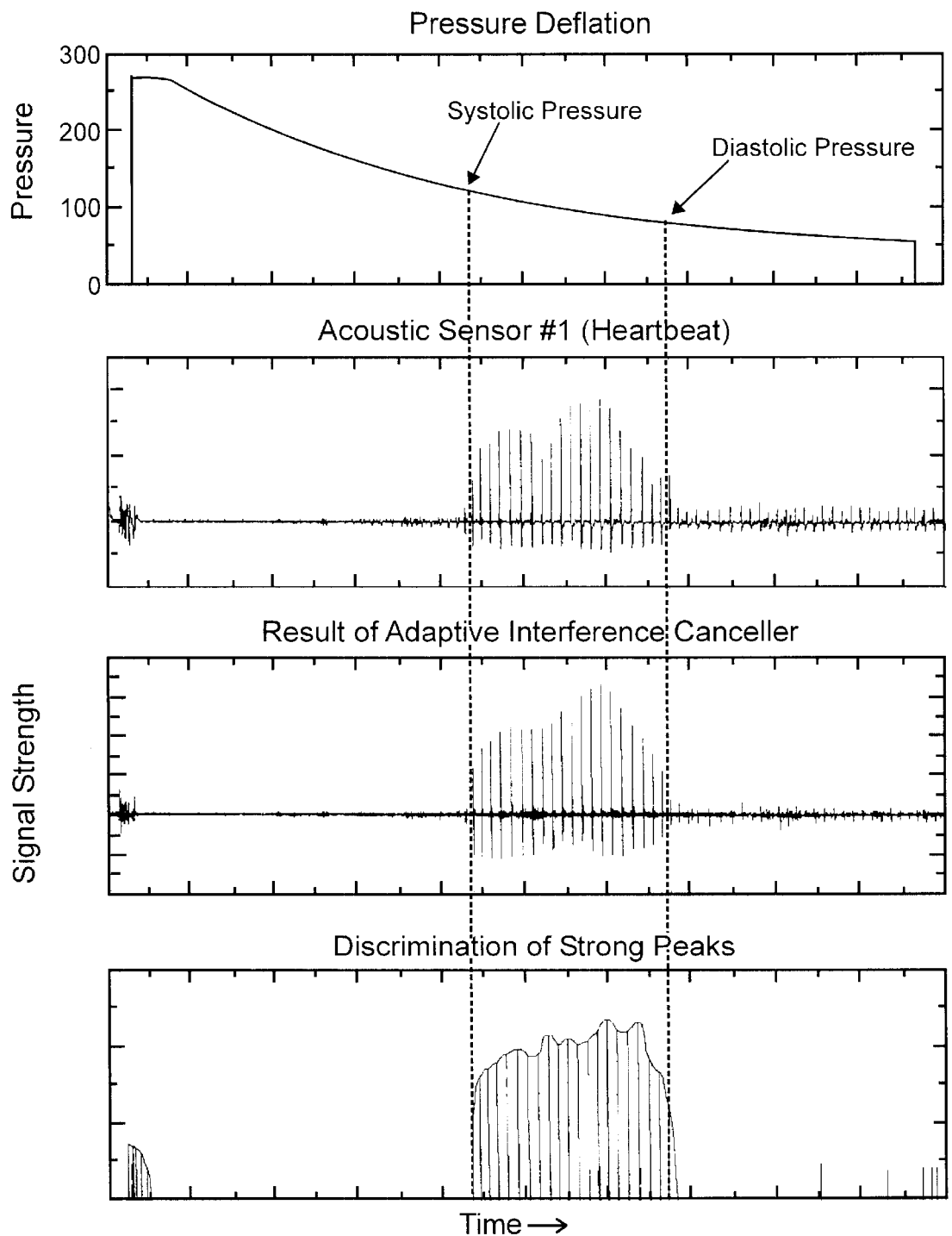
FIG. 3 illustrates simulated results of the signal processing according the invention in a relatively noiseless environment; and, FIG. 4 illustrates simulated results of the signal processing according the invention in presence of intense noise and vibrations.

FIG. 3 shows results of the device and method for measuring blood pressure and heart rate according to the invention in an almost noiseless environment. The top curve indicates pressure deflation of the pressure cuff 1 as function of time. The second curve from top shows the acoustic signal measured by the primary acoustic sensor 3. Periodic pulses resulting from the heart beat are clearly visible and the first and last pulse are well defined. The next curve shows the acoustic signal after it has been processed by the adaptive interferer canceller. It is evident that the noise level is lower in this signal and residual heart beats present in the unprocessed signal have been removed. The bottom curve shows the peaks discriminated by the peak discriminator from the noise. Small areas at the beginning and the end are discarded due to their non-periodic nature and the fact that they are not constant over a period that could be deemed to be a series of heart beats. The remaining sequence is retained and used to determine blood pressure and heart rate. In this case the systolic blood pressure is 123 psi, the diastolic blood pressure is 83 psi and the heart rate is 84 beats per minute.

Figure 4:
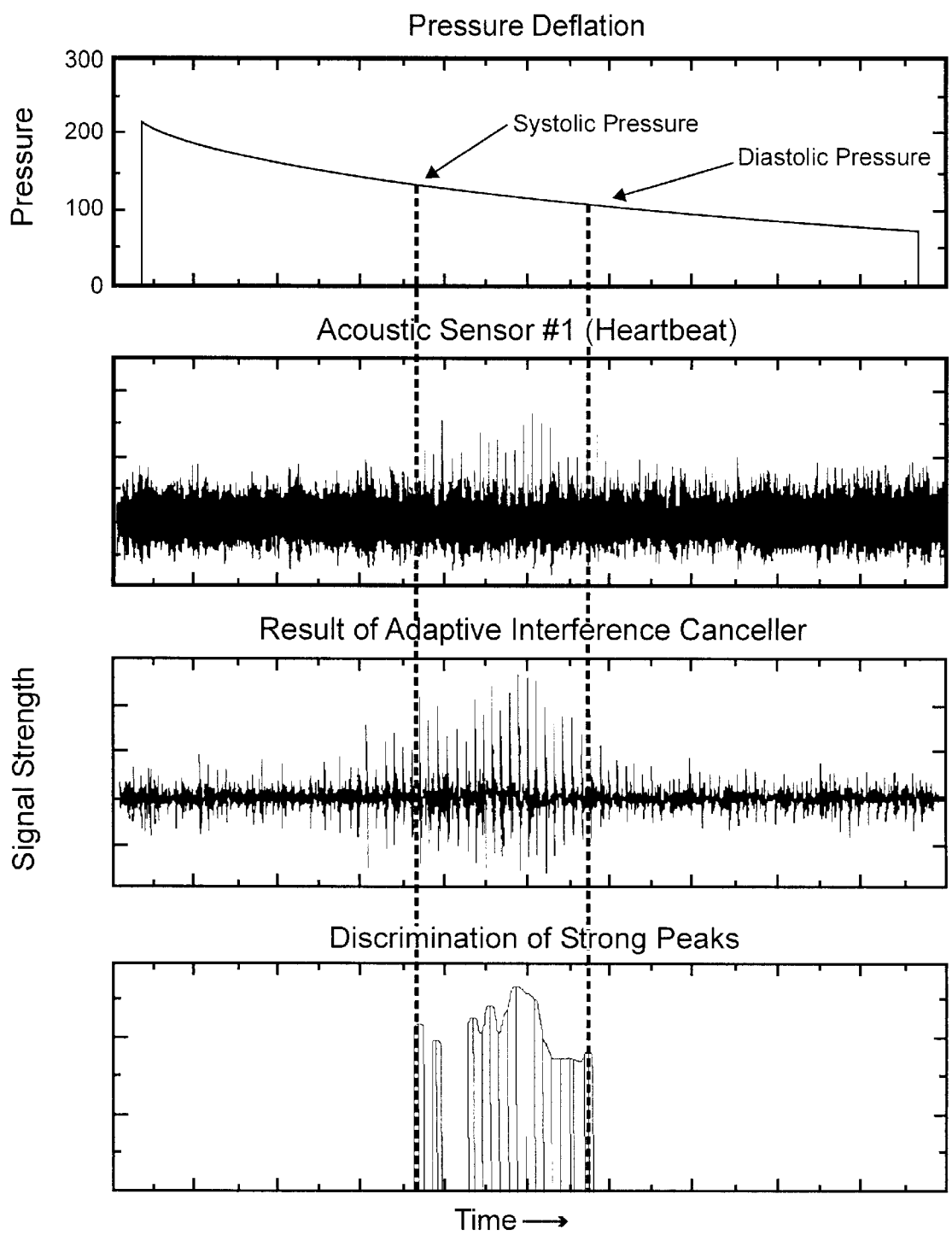

FIG. 4 shows results for measurements taken aboard a helicopter—an environment comprising extreme noise and vibration levels. It is evident that the signal detected by the primary acoustic sensor is very noisy and the first and the last pulse cannot directly be identified. However, after processing the signal using the adaptive interferer canceller and the first stage of the peak discrimination the first and the last pulse are readily identified. The systolic and diastolic blood pressures are 132 psi and 108 psi, respectively, and the heart rate is 92 beats per minute. These measurements, as well as those taken under noiseless conditions compare favorably with measurements taken by the traditional method immediately before the experiments using the device according to the invention.

The device and method for measuring the blood pressure and heart rate according to the invention is highly advantageous to the prior art by providing good results in environments with extreme levels of noise and vibration. In many emergency situations it is essential for saving the live of a victim to obtain accurate measurements of blood pressure and heart rate in order to provide first emergency treatment. Unfortunately, in many cases this has to be done in a very noisy environment such as an ambulance, a helicopter or a naval vessel. This invention provides the means to obtain accurate results under such conditions and allows measurements of blood pressure and heart rate even if the victim is under cardiogenic shock. The signal processing requires only a minimum of computation, therefore, the device for measuring blood pressure and heart rate may be battery operated and assembled in a small portable housing. For example, such a device allows measurement of the blood pressure while the victim is transported on a stretcher to an ambulance, thus saving valuable time.

In another embodiment the device according to the invention is used to monitor the heart rate during transportation. In this case the pressure cuff 1 is inflated only slightly above the diastolic pressure in order to be able to detect the heart beat but not to interrupt the blood flow through the artery.

Of course, numerous other embodiments may be envisaged without departing from the spirit and scope of the invention.

What is claimed is:

1. A method for measuring systolic and diastolic blood pressure of a patient comprising the steps of:
   sensing blood pressure signals corresponding to heart beat using a first acoustic sensor placed on the patient near a location of an artery of the patient, the first acoustic sensor for producing a first acoustic signal in dependence upon the blood pressure signals;
   sensing noise and vibrations using a second acoustic sensor for producing a second acoustic signal in dependence upon noise and vibrations, the second sensor being placed at a location away from an artery such that the second acoustic signal enables reliable signal processing for measuring systolic and diastolic blood pressure using non-linear adaptive interference cancellation;
   sensing pressure applied to the artery using a pressure transducer for sensing pressure and for providing a pressure signal in dependence upon the sensed pressure;
   providing the first acoustic signal, the second acoustic signal and the pressure signal to a processing unit while the pressure is applied to the artery;
   processing the first acoustic signal for removing interference due to noise and vibrations in the first acoustic signal by subtracting the second acoustic signal from the first acoustic signal using the adaptive interference cancellation;
   detecting heart beat pulses within the processed first acoustic signal; and,
   determining systolic and diastolic pressure by relating the detected heart beat pulses to the pressure signal.

2. A method for measuring systolic and diastolic blood pressure of a patient as defined in claim 1, comprising the steps of:
   applying pressure to the artery such that the artery is forced closed; and,
   reducing the pressure applied to the artery.

3. A method for measuring systolic and diastolic blood pressure of a patient as defined in claim 2, comprising the step of:
   sensing the blood pressure signals while performing the step of applying pressure to the artery until the artery is forced closed.

4. A method for measuring systolic and diastolic blood pressure of a patient as defined in claim 2, wherein the first acoustic sensor is placed near the artery downstream of a location where the pressure is applied to the artery.

5. A method for measuring systolic and diastolic blood pressure of a patient as defined in claim 1, wherein the first acoustic signal is band pass filtered.

6. A method for measuring systolic and diastolic blood pressure of a patient as defined in claim 1, wherein the second acoustic signal is band pass filtered.

7. A method for measuring systolic and diastolic blood pressure of a patient as defined in claim 1, wherein the processed first acoustic signal is band pass filtered.

8. A method for measuring systolic and diastolic blood pressure of a patient as defined in claim 1, wherein the second acoustic signal is processed using an adaptive filter.

9. A method for measuring systolic and diastolic blood pressure of a patient as defined in claim 1, wherein the heart beat pulses are detected using a peak discriminator.

10. A method for measuring systolic and diastolic blood pressure of a patient as defined in claim 9, wherein peaks greater than a floor noise level are isolated.

11. A method for measuring systolic and diastolic blood pressure of a patient as defined in claim 9, wherein peaks not satisfying periodicity and constancy in repetition are discarded.

12. A method for measuring systolic and diastolic blood pressure of a patient as defined in claim 1, comprising the step of:

determining a heart rate from the detected heart beat pulses.

13. A method for monitoring heart beat of a patient within a noisy environment comprising the steps of:

sensing blood pressure signals corresponding to heart beat using a first acoustic sensor placed on the patient near a location of an artery of the patient, the first acoustic sensor for producing a first acoustic signal in dependence upon the blood pressure signals;

sensing noise and vibrations using a second acoustic sensor for producing a second acoustic signal in dependence upon noise and vibrations, the second sensor being placed at a location away from an artery such that the second acoustic signal enables reliable signal processing for measuring systolic and diastolic blood pressure using non-linear adaptive interference cancellation;

providing the first acoustic signal and the second acoustic signal to a processing unit; removing interference due to noise and vibrations in the first acoustic signal by subtracting the second acoustic signal from the first acoustic signal using the adaptive interference cancellation;

detecting heart beat pulses within the first acoustic signal; and, determining a heart rate from the detected heart beat pulses.

14. A method for monitoring heart beat of a patient as defined in claim 13, wherein a pressure above diastolic blood pressure is applied to the artery.

15. A method for monitoring heart beat of a patient as defined in claim 14, wherein the first acoustic sensor is placed near the artery downstream of a location where the pressure is applied to the artery.

16. A device for measuring systolic and diastolic blood pressure of a patient in an environment with extreme levels of noise and vibration, the device comprising:

a pressure cuff for applying pressure to an artery of the patient;

a pressure transducer for providing a pressure signal in dependence upon the pressure applied to the artery;

a first acoustic sensor for producing a first acoustic signal in dependence upon blood pressure signals corresponding to heart beat;

a second acoustic sensor for producing a second acoustic signal in dependence upon noise and vibration, the second sensor being placed such that the second acoustic signal enables reliable signal processing for measuring systolic and diastolic blood pressure using non-linear adaptive interference cancellation; and, a processing unit for processing the first acoustic signal using the second acoustic signal using the adaptive interference cancellation, for detecting heart beat pulses within the processed first acoustic signal and for determining systolic and diastolic blood pressure using the detected heart beat pulses and the pressure signal.

17. A device for measuring systolic and diastolic blood pressure of a patient in an environment with extreme levels of noise and vibration as defined in claim 16, wherein the processing unit is used for determining a heart rate from the detected heart beat pulses.

18. A device for measuring systolic and diastolic blood pressure of a patient in an environment with extreme levels of noise and vibration as defined in claim 16, comprising a band pass filter for filtering the first and the second acoustic signal.

19. A device for measuring systolic and diastolic blood pressure of a patient in an environment with extreme levels of noise and vibration as defined in claim 16, comprising a band pass filter for filtering the processed first acoustic signal.

* * * * *